United States Patent [19]

Kusakabe et al.

[11] Patent Number: 5,017,561
[45] Date of Patent: May 21, 1991

[54] ANTIBOTIC 6270B AND ITS USE AS AN ANTICOCCIDIOSIS AGENT AND A FEED ADDITIVE

[75] Inventors: Yoko Kusakabe, Tokorozawa; Hiroshi Suzuki, Fujieda; Hidehiko Kudo, Kashiwa, all of Japan

[73] Assignee: Kaken Pharmaceutical Co., Ltd., Tokyo, Japan

[21] Appl. No.: 199,849

[22] Filed: May 27, 1988

[30] Foreign Application Priority Data

May 30, 1987 [JP] Japan ................. 62-133492

[51] Int. Cl.$^5$ ................. A61K 31/71; C07H 15/04
[52] U.S. Cl. ................. 514/25; 536/16.8; 536/18.1
[58] Field of Search ................. 536/16.8, 18.1; 514/25

[56] References Cited

U.S. PATENT DOCUMENTS 4,582,822  4/1986  Hamill et al. ................. 514/25

FOREIGN PATENT DOCUMENTS 0158179  10/1985  European Pat. Off. .

Primary Examiner—Johnnie R. Brown
Assistant Examiner—Elli Peselev

Attorney, Agent, or Firm—Oblon, Spivak, McClelland, Maier & Neustadt

[57] ABSTRACT

An antibiotic 6270B having the formula:

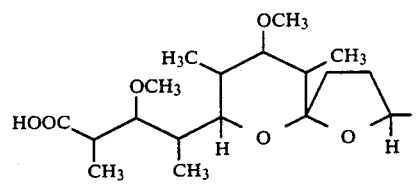

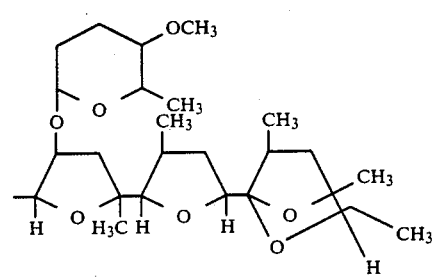

and a salt thereof.

6 Claims, 3 Drawing Sheets

ANTIBOTIC 6270B AND ITS USE AS AN ANTICOCCIDIOSIS AGENT AND A FEED ADDITIVE

The present invention relates to a novel antibiotic 6270B, processes for its production, and its use as an anticoccidiosis agent or as a feed additive to accelerate the growth of domestic animals or fowls.

The present inventors have isolated a number of microorganisms from various soils for the purpose of searching new antibiotics and studied the antibiotics produced by the isolated microorganisms. As a result, they have found that when a microorganism belonging to the genus Nocardiopsis isolated from soil collected in Abashiri city, Hokkaido, Japan, is cultured in a proper culture medium, an antibiotic 6270 having a high antibacterial activity against gram positive bacteria is accumulated in the culture medium (Japanese Unexamined Patent Publication No. 217896/1985).

From a further study of the metabolite of the microorganism, it has been found that a new antibiotic is present which is different from the antibiotic 6270. This antibiotic was isolated and examined for the physicochemical properties and biological properties, whereby it has been confirmed to be a new antibiotic and named an antibiotic 6270B.

It has also been found that the antibiotic 6270B can be prepared also by subjecting the antibiotic 6270 to chemical treatment.

The present invention is based on these discoveries, and provides the new antibiotic 6270B and processes for its production, and its use as an anticoccidosis agent or as a feed additive to accelerate the growth of domestic animals or fowls.

Namely, the present invention provides an antibiotic 6270B having the formula:

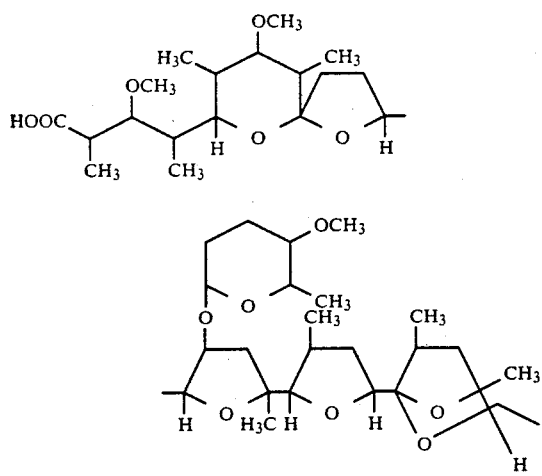

and a salt thereof The antibiotic 6270B has the stereostructural formula:

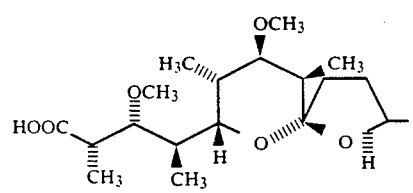

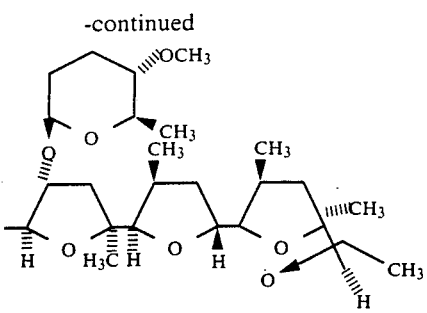

The antibiotic 6270B can be prepared by a process which comprises culturing an antibiotic 6270B-producing microorganism belonging to the genus Nocardiopsis and isolating the antibiotic 6270B from the culture product.

The antibiotic 6270B can be prepared also by a process which comprises boiling a solution of an antibiotic 6270 in free acid form in an organic solvent and isolating the antibiotic 6270B from the solution Further, the present invention provides an anticoccidiosis agent which contains the antibiotic 6270B as the active ingredient, and a method for preventing and curing coccidiosis of domestic fowls and animals which comprises administering an effective amount of the antibiotic 6270B to the domestic fowls and animals.

Furthermore, the present invention provides a growth accelerating and feed efficiency increasing agent for domestic animals and fowls, which comprises the antibiotic 6270B as the effective ingredient, and a method for accelerating the growth of domestic animals and fowls and increasing the feed efficiency thereof, which comprises administering an effective amount of the antibiotic 6270B to the animals and fowls. Accordingly, the present invention provides a feed of domestic animals and fowls, which contains an effective amount of the antibiotic 6270B. The effective amount in this respect is usually from 0.5 to 200 ppm, preferably from 1 to 100 ppm.

Now, the present invention will be described in detail with reference to the preferred embodiments.

In the accompanying drawings, FIG. 1 is the infrared absorption spectrum of the antibiotic 6270B as measured by means of potassium bromide tablet.

Figure 1:
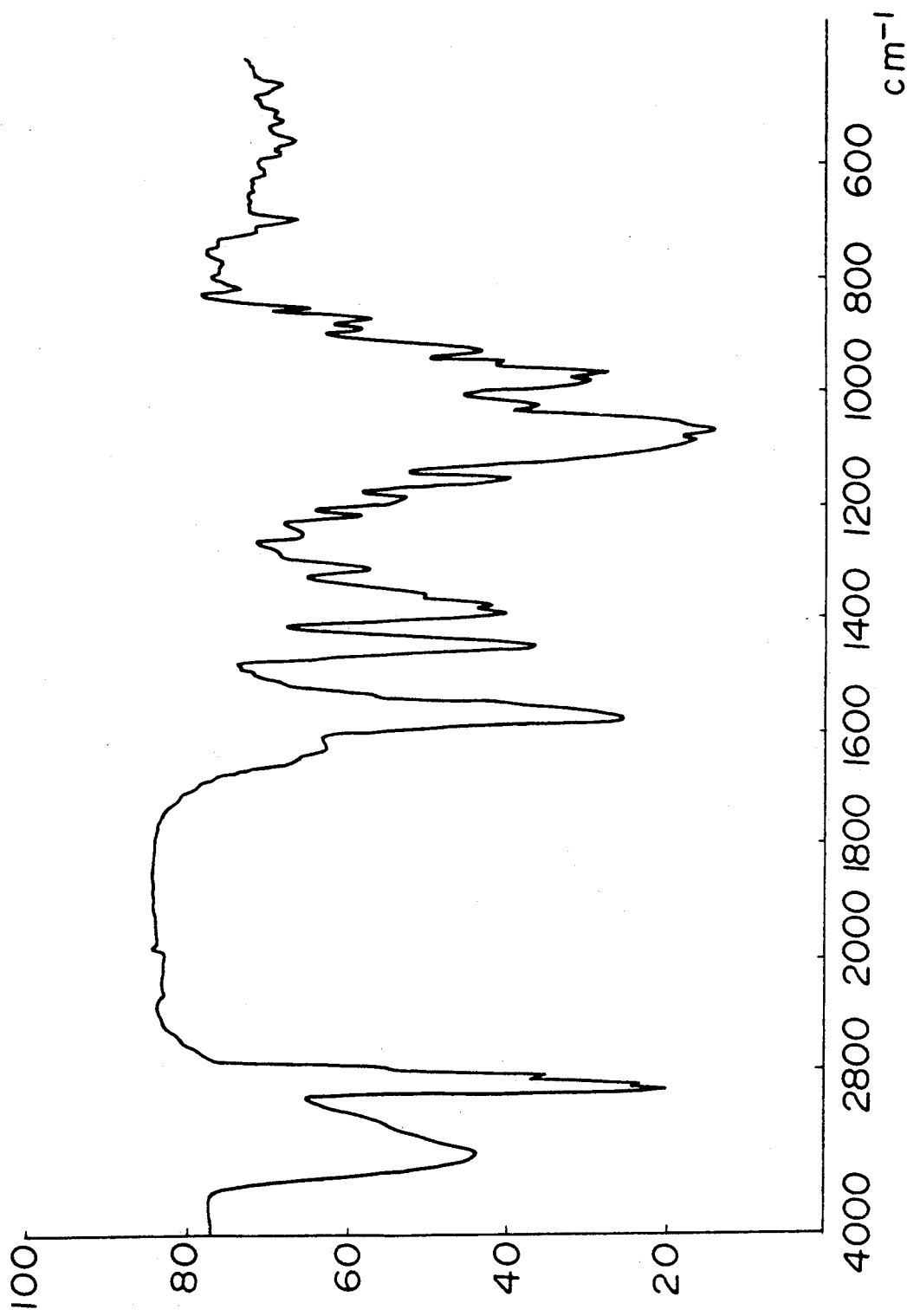

The microorganism which may be employed for the production of the antibiotic 6270B, may be any microorganism belonging to genus Nocardiopsis so long as it is capable of producing the antibiotic 6270B. However, it is preferred to employ Nocardiopsis sp. 6270 strain isolated previously by the present inventors (deposited in Fermentation Research Institute of Japan as FERM BP-717) (Japanese Unexamined Patent Publication No. 217896/1985).

In carrying out the process of the present invention, the antibiotic 6270B-producing microorganism may be cultured in accordance with the conventional methods for cultivation of known actinomyces. However, from the industrial viewpoint, it is advantageous to employ a method of cultivation with aeration-agitation. As the culture medium for the production, there may be employed materials which are commonly used for the cultivation of actinomyces. Namely, various carbon sources, nitrogen sources and organic or inorganic salts, as well as a defoaming agent, if necessary, may be used in a suitable combination. For instance, as the carbon sources, there may be used glucose, starch, glycerol, dextrin, sucrose and animal or vegetable oils. As the nitrogen sources, there may be employed soybean meal, corn steep liquor, wheat embryo, and ammonia. Further, if necessary, inorganic salts such as calcium carbonate, sodium chloride, potassium chloride, and phosphates may be added. It is also possible to add organic or inorganic salts having an action to assist the growth of the microorganism and thereby facilitate the production of the antibiotic 6270B. The temperature for the cultivation is usually within a range of from 25° to 35° C., preferably around 30° C. The cultivation time may vary depending upon the various conditions. However, usually the accumulation of the produced antibiotic 6270B reaches to the maximum within from 72 to 148 hours.

The antibiotic 6270B may be isolated from the culture medium and purified by utilizing its physicochemical properties by means of conventional methods such as a method of utilizing the difference in the solubility from impurities, a method of utilizing the difference in the adsorption to ion exchange resins or various adsorbing agents, a method of extracting with an organic solvent immiscible with water, or a proper combination of various means such as precipitation, removal of impurities, dialysis, drying and recrystallization.

For instance, the antibiotic 6270B produced in the culture medium may preferably be recovered as follows. After addition of a filter aid such as diatomaceous earth or Radiolite 700, the culture broth is filtered, and the filtrate and the microbial cells are respectively extracted with suitable solvents such as ethyl acetate and acetone. Then, the cell extract and the filtrate extract are combined. The solvent is distilled off from this extract solution, whereby the antibiotic 6270 and the antibiotic 6270B are obtained as crude crystals. In order to isolate the antibiotic 6270B from the crude crystals, the crude crystals are subjected to, for example, chromatography. The eluate containing the antibiotic 6270B is concentrated under reduced pressure, and the residue is dissolved in a suitable solvent such as ethyl acetate and then treated with a dilute hydrochloric acid. The solvent layer is washed with water, treated with a dilute sodium carbonate aqueous solution and concentrated, whereby the antibiotic 6270B crystallizes as sodium salt.

The sodium salt-type antibiotic 6270B thus obtained can be recrystallized from a suitable solvent such as n-hexane/ethyl acetate or ethyl acetate/ethanol/water to obtain pure crystals.

The antibiotic 6270B can be prepared also by dissolving the antibiotic 6270 in free acid form in an organic solvent such as methanol and boiling this solution for a few hours under reflux.

The reaction solution thus obtained is concentrated, and the concentrated solution is subjected to e.g. chromatography. The eluted fractions containing the antibiotic 6270B are combined and concentrated under reduced pressure. Then, the residue is dissolved in an organic solvent such as ethyl acetate and then treated with a dilute hydrochloric acid solution and then with a dilute sodium carbonate aqueous solution. The solvent layer is then concentrated to obtain the antibiotic 6270B in the form of sodium salt.

The sodium salt-type antibiotic 6270B thus obtained can be recrystallized from a suitable solvent such as n-hexane/ethyl acetate or ethyl acetate/ethanol/water to obtain pure crystals. The sodium salt-type antibiotic 6270B thus obtained has the following properties:

(1) Colorless prismatic crystals; per se acidic substance
(2) Melting point: 125°–127° C.
(3) Elemental analysis (Found %): C: 62.37%, H: 8.93%; 0: 26.09%; Na: 2.48%
(4) Specific rotation: $[\alpha]^{25}_D - 24.0°$ (C 1.0, methanol)
(5) Ultraviolet absorption spectrum: The maximum absorption bands not observed at 210 nm or more, as measured in the ethanol solution
(6) Characteristic absorption ($cm^{-1}$) in the infrared absorption spectrum (taken with the potassium bromide tablet): 3450, 2960, 2945, 2870, 1580, 1450, 1400, 1380, 1315, 1220, 1160, 1095, 1075, 990, 978 (The absorption spectrum is shown in FIG. 1.)
(7) Solubility: Soluble in methanol, ethanol, ethyl acetate, chloroform, ethyl ether, acetone, and benzene; insoluble in water
(8) Color reactions: Positive in the vanilline-sulfuric acid reaction and the Dragendorff reaction; negative in the ninhydrin reaction; colors with I gas
(9) Thin layer chromatography (by means of Kieselgel $GF_{254}$, manufactured by Merck Co.):

| Solvent system | Rf value |
|---|---|
| Chloroform-methanol (20:1) | 0.15 |
| Benzene-ethyl acetate (1:1) | 0.06 |
| Benzene-acetone (1:1) | 0.31 |
| Chloroform-acetone (2:1) | 0.10 |
| Ethyl acetate | 0.28 |

Figure 2:
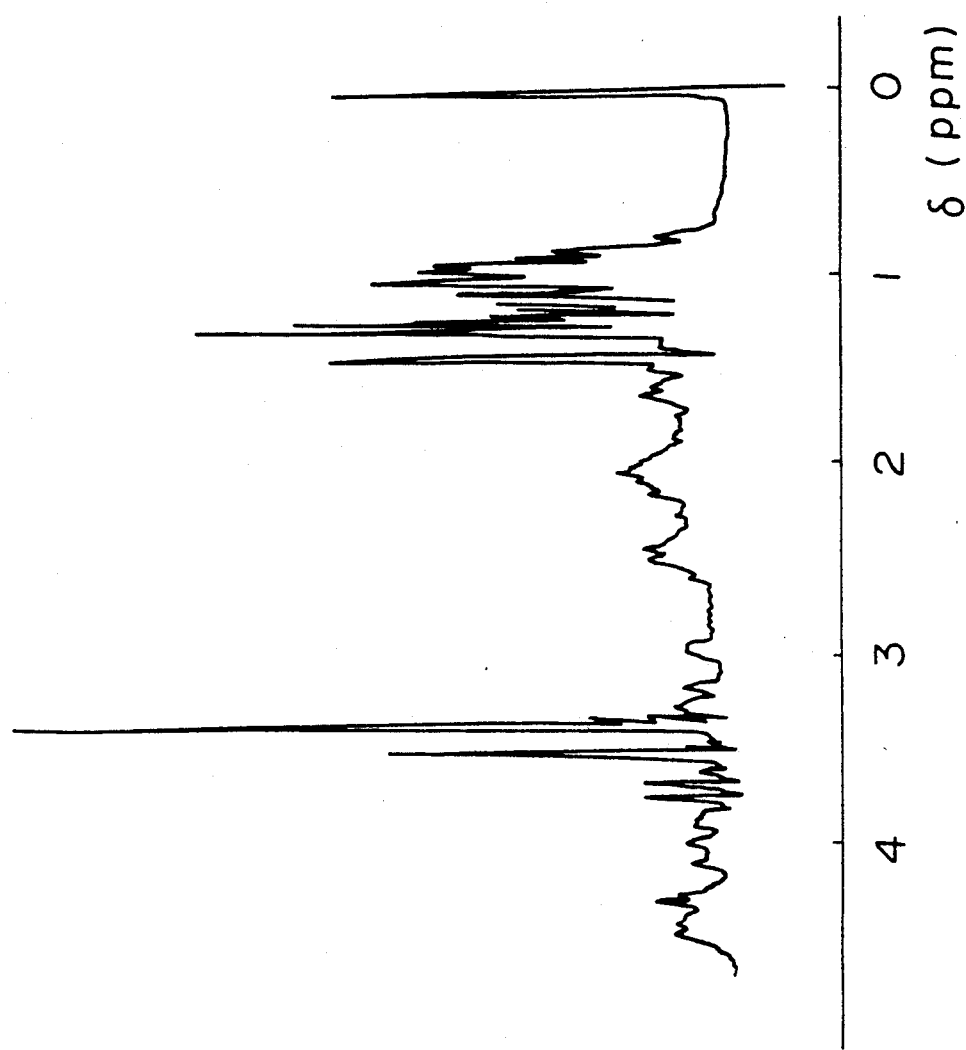
FIG. 2 is the $^1$H-NMR spectrum of the antibiotic 6270B as measured in heavy chloroform by using TMS as internal standard.
Figure 3:
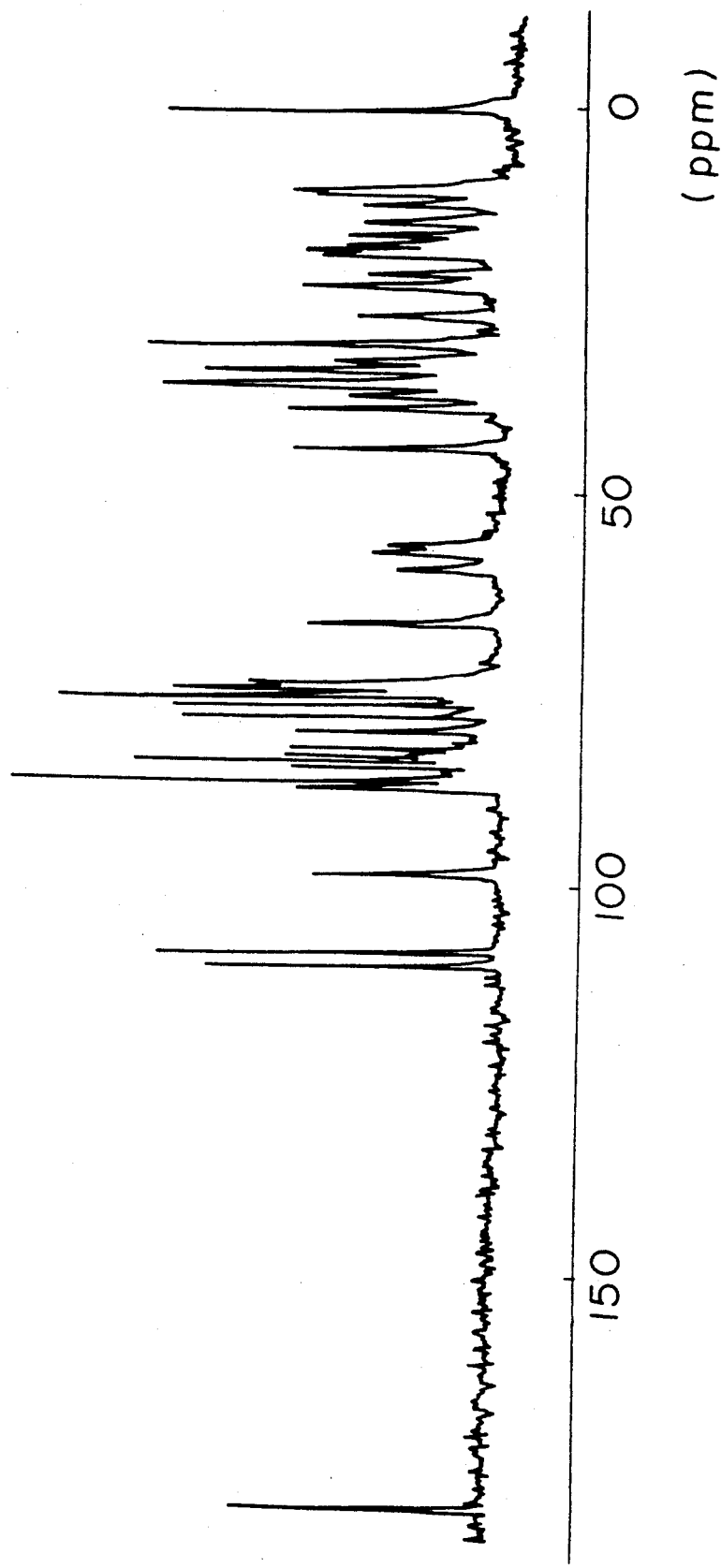
FIG. 3 is the $^{13}$C-NMR spectrum of the antibiotic 6270B as measured in heavy chloroform by using TMS as internal standard.

(10) $^1$H-NMR spectrum: The presence of three methoxyl groups was observed at ppm 3.24 (6 H), 3.40 (3 H), as measured at 100 MHz in heavy chloroform by using TMS as internal standard (The spectrum is shown in FIG. 2.)
(11) $^{13}$C-NMR spectrum: the results of the measurement in heavy chloroform by using TMS as internal standard, are shown in FIG. 3.
(12) The antibacterial spectrum is shown in Table 1.

TABLE 1

| Test microorganism | Minimum inhibitory concentration (mcg/ml) |
|---|---|
| Staphylococcus aureus FDA209P JC-1 | 6.25 |
| Staphylococcus aureus Terajima | 12.5 |
| Streptococcus pyogenes Cook | 0.78 |
| Micrococcus luteus ATCC 9341 | 12.5 |
| Bacillus subtilis ATCC 6633 | 12.5 |
| Escherichia coli NIHJ JC-2 | >100 |
| Klebsiella pneumoniae PCI 602 | >100 |
| Salmonella typhi 901 | >100 |
| Serratia marcescens IAM 1184 | >100 |
| Pseudomonas aeruginosa IFO-3445 | >100 |
| Proteus vulgaris OX-19 | >100 |
| Enterobacter aerogenes ATCC 13048 | >100 |

Note:
The culture medium used was "Nissui" culture medium N for discs for sensitivity tests (manufactured by Nippon Seiyaku K. K.)

From the foregoing physicochemical and biological characteristics, this substance has been confirmed to belong to a general class of antibiotics called polyethers.

This substance is assumed to have three methoxyl groups in a molecule from the $^1$H-NMR spectrum. As known antibiotics having three methoxy groups in one molecule, among the polyether antibiotics, there may be mentioned antibiotic 6270 (Japanese Unexamined Patent Publication No. 217896/1985), C20-12 (Japanese Unexamined Patent Publication No. 53919/1983), A-204B (Handbook of Microbiology 410, vol. 3, CRC Press), T-42082 (Japanese Unexamined Patent Publication No. 79730/1976), T-40517 (Japanese Unexamined Patent Publication No. 105811/1975), 38295 (Japanese Unexamined Patent Publication No. 125793/1976), No. 6016 (Japanese Unexamined Patent Publication No. 84576/1979), X-14868C (Japanese Unexamined Patent Publication No. 120696/1981), CP-47433 (Japanese Unexamined Patent Publication No. 154188/1982), CP-47434 (Japanese Unexamined Patent Publication No. 154187/1982) and LL-C23024 (Japanese Unexamined Patent Publication No. 78598/1983).

However, the 6270B antibiotic differs from these known substances in the characteristics such as the melting point, specific rotation, elemental analytical values or infrared absorption spectrum, and is apparently a new antibiotic.

The antibiotic 6270B has particularly strong antibacterial effects against gram-positive bacteria, and is useful as an antibacterial agent.

Further, it has anticoccidiosis, acaricidal and antiviral activities at a low concentration, and it is useful as anticoccidiosis agent of domestic fowls such as chicken, quail, duck, goose and turkey, and domestic animals such as cattle, swine, rabbit, buffalo, goat and sheep, as an agent for treating diarrhea of domestic animals, or as an agent to increase feed efficiency or to accelerate the growth of domestic animals and fowls.

Now, the present invention will be described in further detail with reference to Examples. However, it should be understood that the present invention is by no means restricted to these specific Examples.

EXAMPLE 1

Nocardiopsis sp. 6270 strain (FERM BP-717) was inoculated to 1 liter of a culture medium (pH 6.0) comprising 6.0% of glucose, 2.0% of soybean mean, 1.0% of torula yeast and 0.5% of calcium carbonate, and cultivated at 30° C. for 48 hours. This culture broth was inoculated to 100 liters of a culture medium having the same composition as above, and cultured at 30° C. for 96 hours under stirring and aeration in a tank having a capacity of 200 liters. The rate of aeration was 100 liters per minute, and the rotation of the stirrer was 250 rpm. After addition of a filter aid (Radiolite 700, trademark) this culture broth was filtered to separate the filtrate and cells. Then, the filtrate was extracted with 40 liters of ethyl acetate, and the cells were extracted with 30 liters of acetone. The acetone extract of the cells was concentrated under reduced pressure to remove acetone, and extracted with 20 liters of ethyl acetate. This extract was combined with the extract from the filtrate, and the combined solution was concentrated under reduced pressure The residue was adsorbed on a column of 750 g of silica gel (Wako gel C-200, tradename) packed with chloroform, and a mixture of chloroform and methanol (100:1) was passed through the column. The active fraction was concentrated under reduced pressure to dryness, whereby an oily residue was obtained. Then, the residue was dissolved in a small amount of acetone, and the solution was adsorbed on a column of Sephadex LH-20 filled with acetone, and eluted with acetone. The active fraction thereby obtained was concentrated to obtain a mixture of crude crystals of the antibiotic 6270 and the antibiotic 6270B.

In order to isolate the antibiotic 6270B from the mixture of crude crystals, the mixture is subjected to silica gel column chromatography. Namely, the crude crystals were dissolved in a solvent mixture of ethyl acetate/n-hexane (3/1) and adsorbed on a column of 300 g of silica gel packed by means of n-hexane. Then, the elution was conducted with the same solvent mixture, whereby the antibiotic 6270B eluted first and then the antibiotic 6270 eluted.

The detection and determination of these substances were made by the antibacterial activities as measured by means of an agar plate of Bacillus subtilis and by the silica gel thin layer chromatography.

The antibiotic 6270B fraction thus obtained was shaken with dilute hydrochloric acid. Then, the ethyl acetate layer was washed with water and then shaked with a dilute sodium carbonate aqueous solution. Then, ethyl acetate layer was concentrated under reduced pressure.

The formed crystals are recrystallized from n-hexane, ethyl acetate, whereby 0.6 g of sodium salt of the antibiotic 6270B was obtained as colorless prismatic crystals. The sodium salt of the antibiotic 6270B thus obtained exhibited the above-mentioned physicochemical and biological characteristics.

EXAMPLE 2

5 g of the antibiotic 6270 (free acid form) was dissolved in 250 ml of methanol, and the solution was boiled for 4 hours under reflux. After completion of the reaction, the solution was adjusted to pH 9 with an aqueous sodium hydroxide solution and then concentrated. The redidue was dissolved in a small amount of a solvent mixture of acetone/methanol (2/1) and adsorbed on a column of 90 g of active alumina packed by means of the same solvent mixture. Then, the elution of the antibiotic 6270B from the column was conducted while increasing the methanol concentration of the solvent mixture from (2:1) to (1:1).

The detection and determination of the substance were made by the antibacterial activities by means of an agar plate of Bacillus subtilis and by the silica gel thin layer chromatography. The active fractions of the antibiotic 6270B were put together and concentrated. The residue was crystallized from n-hexane/ethanol/water to obtain 1.65 g of colorless prismatic crystals.

The sodium salt of the antibiotic 6270B thus obtained exhibited the above-mentioned physicochemical and biological characteristics.

Test Example 1: Anticoccidiosis Activity

Tested Agent and Feed

The antibiotic 6270B was uniformly mixed with a perfect combination feed for chicks (manufactured by Oriental Yeast Co.) to obtain a predetermined concentration. The feed thus obtained was freely taken by chickens from two days before the inoculation of oocyst to the end of the test (eight days after the infection).

As a comparative agent, Salinomysin was used which is known to be an anticoccidiosis agent.

Chickens Used

Chickens used in this test were healthy cocks of egg-laying fowl (Shever Starcross) which were 7 days old (9 days old when infected) and had been bred under the conditions of perfect prevention of coccidiosis infection. Every group had five chickens. Oocyst inoculated and the quantity of inoculation:

The oocyst used for the infection was a sensitive strain of *Eimeria tenella*. Every chicken was inoculated to the crop with full grown oocysts ($3 \times 10^4$), orally by using metal zonde.

Judgement of Effect

The effect of the agents was determined by the Anticoccidial Index (ACI) which was calculated by the following formula:
ACI = (Relative increase in weight + Survival rate) − (Oocyst value + Disease value)
120 or less: Not effective as an anticoccidiosis agent.
160 or less: Slightly effective as an anticoccidiosis agent.
160–180: Moderately effective as an anticoccidiosis agent.
180 or higher: Extremely effective as an anticoccidiosis agent.

(i) Relative increase in weight

At the end of the test, the increase in weight (i.e. the weight at the end of the test—the weight at the time of infection) of each test group was measured and the relative increase in weight was calculated based on the weight of the control group (100) which were bred with the anticoccidiosis agent free feed and not inoculated.

(ii) Oocyst index

The number of oocyst in the caecum was counted on 8 days after the inoculation by homogenizing the intestinal canal. The oocyst index was defined as follows:

| The number of oocyst found in the intestinal canal | The oocyst index |
| --- | --- |
| $0.0–0.1 \times 10^6$ | 0 |
| $0.1–1.0 \times 10^6$ | 1 |
| $2.0–5.0 \times 10^6$ | 10 |
| $6.0–11.0 \times 10^6$ | 20 |
| $>11.0 \times 10^6$ | 40 |

(iii) Disease index of the intestinal canal

The chickens tested were anatomized at the end of the test (8 days after the infection), and the intestinal canal was examined with the naked eye to determine the disease index. The disease index was defined as follows and the disease value was defined ten times as many as the value of the disease index.

0, (−) The caecum is quite normal. If bleeding spot is found, (−) is changed to (+).

1, (+) The caecum is normal in shape. The content therein is slightly fluid and yellowish. Slight swelling is found partly on a mucous membrane of the caecum which becomes whitish.

2, (++) The caecum is generally normal in shape. Swelling is found on the whole surface of a mucous membrane No bleeding is found in the content. Mucus is slightly yellowish and faded. A few white spot-like necroses or bleeding spots are found in a mucous membrane.

3, (+++) The caecum is clearly withered and changed in shape, and is a little longer than the rectum. The content is quite abnormal and is often filled with coagulated blood or white-gray, cheese-like degenerated mater. The wall of the caecum is clearly swelled and easily broken and sometimes bleeding spots still remain. The disease reaches a basis of the caecum but not the rectum.

4, (++++) Withering and deformation of the caecum are remarkable. The caecum looks like a sausage in shape and is not longer than the rectum. The disease reaches almost one third or fourth of the rectum.

Groups 1 to 3 were fed with the feed containing a predetermined concentration of the antibiotic 6270B from two days prior to the inoculation of oocyst. Group 4 was fed with the feed containing the antibiotic Salinomysin as a comparative agent. Group 5 is the infected non-treated control group inoculated with oocyst and fed with the basic feed containing no anticoccidiosis agent. Group 6 is a non-infected, non-treated control group.

The results are shown in Table 2.

TABLE 2

| Group | Antibiotic | Dose (ppm) | Weight increase (%) | Degree of bloody excrement* | | | | | Survival rate (%) |
| | | | | 4 days | 5 days | 6 days | 7 days | 8 days | |
| --- | --- | --- | --- | --- | --- | --- | --- | --- | --- |
| 1 | 6270 B | 25 | 90.3 | − | + | + | − | − | 100 |
| 2 | 6270 B | 50 | 86.4 | − | − | − | − | − | 100 |
| 3 | Salinomysin | 50 | 97.4 | − | − | + | − | − | 100 |
| 4 | Infected non-treated group | 0 | 67.7 | ++ | ++++ | ++++ | + | − | 100 |
| 5 | Non-infected, non-treated group | 0 | 100.0 | − | − | − | − | − | 100 |

| Group | Average number of oocyst in the intestinal canal | Oocyst index | Disease index of the intestinal canal | | | | | Disease value | A.C.I. |
| | | | ++++ | +++ | ++ | + | − | | |
| --- | --- | --- | --- | --- | --- | --- | --- | --- | --- |
| 1 | $5.89 \times 10^5$ | 1 | 0 | 0 | 1 | 4 | 0 | 12 | 177.3 |
| 2 | 0 | 0 | 0 | 0 | 0 | 4 | 1 | 8 | 178.4 |
| 3 | $1.72 \times 10^6$ | 10 | 0 | 1 | 0 | 4 | 0 | 14 | 173.4 |
| 4 | $7.27 \times 10^6$ | 20 | 5 | 0 | 0 | 0 | 0 | 40 | 107.7 |
| 5 | 0 | 0 | 0 | 0 | 0 | 0 | 5 | 0 | 200.0 |

*Degree of bloody excrement:
−: No bloody excrement
+: Less than 10%
++: 10–30%
+++: 30–50%
++++: More than 50%

From these test results, it is evident that the antibiotic 6270B has an anticoccidiosis activity.

Test Example 2: Feed Efficiency Test on Swine

Pigs used: crossbred of Yorkshire species and Landrace species

Basic feed:

A feed comprising 75.85% of corn, 19.50% of soybean cake, 2.60% of fish powder, 1.00% of potassium phosphate, 0.60% of calcium carbonate, 0.25% of sodium chloride and 0.20% of vitamins and minerals (dry provisions: 87.3%, crude proteins: 17.5%, crude fat: 2.1%, crude fiber: 3.5%, crude ash content: 4.1%, energy: 4,140 cal/g) was used as the basic feed.

Test Method:

Fifteen young pigs of 15 kg in an average were divided into three groups, each group consisting of five pigs, so that the average weight would be substantially equal. The antibiotic 6270B was added to the basic feed in an amount of 0, 25 and 50 ppm, respectively. And then the three groups of pigs were fed with the feeds, respectively, for 10 weeks. Then, the body weight and the feed consumption were measured.

The results are shown in Table 3.

TABLE 3

| Group | Amount of antibiotic 6270$^B$ added to the feed (ppm) | Average weight at the initiation of the test (kg) | Average weight increase during the period (kg) | Average amount of feed ingested during the test period (kg) | Feed* demand index | Improvement of** the feed demand index (%) |
|---|---|---|---|---|---|---|
| 1 | 0 | 15.3 | 52.0 | 140.5 | 2.70 | — |
| 2 | 25 | 15.5 | 57.3 | 145.3 | 2.54 | 5.9 |
| 3 | 50 | 15.1 | 58.9 | 147.6 | 2.51 | 7.0 |

*Feed demand index = $\frac{\text{Average amount of feed ingested during the test period}}{\text{Average weight increase during the test period}}$

**Improvement in the feed demand index (%) = $\left(1 - \frac{\text{Feed demand index when 6267 was added}}{\text{Feed demand index when no antibiotic was added}}\right) \times 100$ The feed demand index was improved by from 6 to 7% by feeding the feed containing the antibiotic 6270B. The weight increase was improved by from 10 to 13%.

Test Example 3: Feed Efficiency of Ruminant

Steers used: Holstein (castrated steers of 8 months old)

Concentrated feed:

A commercially available blend feed for beef (concentrated feed) containing at least 11.5% of crude proteins, at least 2.0% of crude fat, at most 9.0% of crude fiber, at most 9.0% of crude ash content, at least 0.7% of calcium, at least 0.4% of phosphorus, at least 9.5% of digestible crude proteins and at least 74.0% in total of digestible nutrients and containing no antibacterial agents such as antibiotics was used as the basic feed.

Test Method:

Fifteen castrated steers of 8 months old were divided into three groups, each consisting of five steers, so that the average body weight will be substantially equal. The antibiotic 6270B was added to the basic concentrated feed in an amount of 0, 15 and 30 ppm, respectively. The three groups of steers were fed with the feeds, respectively, for 310 days. Further, dried rice straw was fed as crude feed in an amount of 1 kg a day per steer The results are shown in table 4.

TABLE 4

| Group | Amount of antibiotic 6270$^B$ added to the feed (ppm) | Average weight at the initiation of the test (kg) | Average weight increase during the period (kg) | Average amount of concentrated feed ingested during the test period (kg) | Concentrated* feed demand index | Improvement of** the concentrated feed demand index (%) |
|---|---|---|---|---|---|---|
| 1 | 0 | 280 | 339 | 2976 | 8.78 | — |
| 2 | 15 | 276 | 356 | 2890 | 8.12 | 7.5 |
| 3 | 30 | 277 | 368 | 2856 | 7.76 | 11.6 |

*Concentrated feed demand index = $\frac{\text{Average amount of feed ingested during the test period}}{\text{Average weight increase during the test period}}$

**Improvement of the concentrated feed demand index (%) = $\left(1 - \frac{\text{Feed demand index when 6267 was added}}{\text{Feed demand index when no antibiotic was added}}\right) \times 100$ The concentrated feed demand index was improved by from 7 to 12% by feeding the feed containing the antibiotic 6270B. The weight increase was improved by from 5 to 9%.

Test Example 4: Toxicity Test

Crj-ICR of male mice of five weeks old (body weight: ±2 g) were used (5 mice per group).

The test sample was suspended in 0.5% methyl cellsolve, and the concentration was adjusted. Then, it was orally adminestered in an amount corresponding to 10 ml/kg of the body weight. The LD$_{50}$ value was calculated by a probit method from the mortality rate upon expiration of 72 hours after the administration and found to be 38.1 mg/kg.

We claim:

1. An antibiotic 6270B having the stereostructural formula:

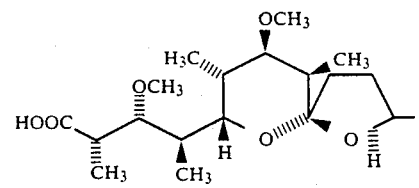

-continued

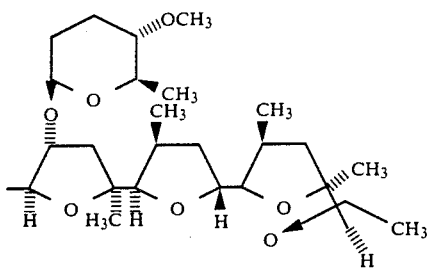

and a pharmaceutically acceptable salt thereof.

2. A method of preventing coccidiosis of domestic fowl and animals, which comprises:
administering a preventively effective amount of antibiotic 2670B as set forth in claim 1 to domestic fowl and animals.

3. A method for accelerating the growth of domestic animals and fowl and of increasing the feed efficiency of domestic animals and fowl, which comprises:
administering a growth accelerating or feed efficiency increasing effective amount of the antibiotic 6270B as set forth in claim 1 to animals and fowl.

4. An anticoccidiosis, growth accelerating or feed efficiency increasing composition, comprising:
a pharmaceutically or physiologically effective amount of the antibiotic 6270B as defined in claim 1 in combination with a pharmaceutically acceptable carrier.

5. A feed for domestic fowl and animals, comprising:
the antibiotic 6270B as set forth in claim 1 in a amount which is physiologically and anticoccidiosisially effective, as a component of feed for fowl and animals.

6. The feed of claim 5, wherein the antibiotic 6270B is present in the feed in an amount of from 0.5 to 200 ppm.

* * * * *